(12) United States Patent
Schlegel et al.

(10) Patent No.: US 7,279,306 B2
(45) Date of Patent: *Oct. 9, 2007

(54) STABLE (FIXED) FORMS OF VIRAL CAPSID PROTEINS, AND VIRAL CAPSID PROTEIN FUSIONS, PREFERABLY PAPILLOMAVIRUS L1 PROTEINS, AND USES THEREOF

(75) Inventors: C Richard Schlegel, Rockville, MD (US); Robert Garcea, Boulder, CO (US)

(73) Assignees: Georgetown University, Washington, DC (US); University of Colorado, Aurora, CO (US)

( * ) Notice: Subject to any disclaimer, the term of this patent is extended or adjusted under 35 U.S.C. 154(b) by 336 days.

This patent is subject to a terminal disclaimer.

(21) Appl. No.: 10/332,037

(22) PCT Filed: Jun. 11, 2001

(86) PCT No.: PCT/US01/18701

§ 371 (c)(1),
(2), (4) Date: Jan. 6, 2003

(87) PCT Pub. No.: WO02/04007

PCT Pub. Date: Jan. 17, 2002

(65) Prior Publication Data

US 2007/0212374 A1    Sep. 13, 2007

Related U.S. Application Data

(60) Provisional application No. 60/216,526, filed on Jul. 6, 2000.

(51) Int. Cl.
*C12P 21/06* (2006.01)
(52) U.S. Cl. .......................................... 435/69.1; 435/6
(58) Field of Classification Search ............. 424/204.1, 424/192.1, 184.1; 435/69.3, 235.1, 6; 530/300
See application file for complete search history.

(56) References Cited

U.S. PATENT DOCUMENTS 5,874,089 A * 2/1999 Schlegel et al. ......... 424/204.1

FOREIGN PATENT DOCUMENTS

| WO | WO93/00436 | * | 1/1993 |
| WO | WO97/05164 | * | 2/1997 |
| WO | WO99/13056 | * | 3/1999 |

OTHER PUBLICATIONS

Li et al, Journal of Virology, 1997, vol. 71, No. 4, pp. 2988-2995.*
Chen et al, Molecular Cell, Mar. 2000, vol. 5, pp. 557-567.*
Steller M. A., Current Opinion in Investigational Drugs, 2002, vol. 3, No. 1, pp. 37-47.*
Icenogle, Joeseph, Analysis of the Sequences of the L1 and L2 Capsid Proteins of Papillomaviruses, Centers for Disease Control, Atlanta, GA, L1 & L2 Capsid Proteins, Ill-74, Oct. 1995. (http://hpv-web.lanl.gov/stdgen/virus/hpv/compendium/htdocs/COMPENDIUM_PDF/95PDF/3/ice.pdf.
De Bruijn et al., "L1-specific protection from tumor challenge elicited by HPV16 virus-like particles," *Virology*, 1998, 250(2): 371-376, (Abstract).
Dupuy et al., "Nasal Immunization of mice with human papillomavirus type 16 (HPV-16) virus-like particles or with the HPV-16 L1 gene elicits specific cytotoxic T lymphocytes in vaginal draining lymph nodes," *Journal of Virology*, 1999, 73(11): 9063-9071.
Liu et al., "Mucosal Immunisation with papillomavirus virus-like particles elicits systemic and mucosal immunity in mice," *Virology*, 1998, 252(1): 39-45, (Abstract).
Nakagawa et al., "T-cell proliferative response to human papillomavirus type 16 peptides: relationship to cervical intraepithelial neoplasia," *Clinical and Diagnostic Laboratory Immunology*, 1996, 3(2): 206-210.
Rudolf et al., "Induction of HPV16 capsid protein-specific human T cell responses by virus-like particles," *Biol. Chem.*, 1999, 380(3): 335-340, (Abstract).
Shepherd et al., "Proliferative T cell responses to human papillomavirus type 16 L1 peptides in patients with cervical dysplasia," *J Gen Virol.*, 1996, 77(Pt 4)L 593-602, (Abstract).

* cited by examiner

*Primary Examiner*—Ali R. Salimi
(74) *Attorney, Agent, or Firm*—Elliot M. Olstein; Raymond J. Lillie (57) ABSTRACT

Novel acetone- or alcohol-fixed viral capsid proteins, bacteria-containing, and papillomavirus L1-GST fusion proteins are described. These proteins are useful in vaccine preparation and as diagnostics.

5 Claims, 7 Drawing Sheets

THROMBIN

L   V   P   R   G   S   P   G   I   P

CTG GTT CCG CGT GGA TCC CCA GGA ATT CCT

EcoRI          COPV L1         Not I

COPV L1 IN pGEX-4T-2 V

GST-L1 DOG STUDY

| | | TUMORS |
|---|---|---|
| GROUP A | 0 ng/ml | 4/4 |
| GROUP B | .125 ng/ml | 4/4 |
| GROUP C | 2.5 ng/ml | 4/4 |
| GROUP D | 50 ng/ml | 4/4* |
| GROUP E | 1,000 ng/ml | 0/4 |

01/19/2000 VACCINATE
02/02/2000 VACCINATE
02/16/2000 CHALLENGE

* SMALL TUMORS

STABLE (FIXED) FORMS OF VIRAL CAPSID PROTEINS, AND VIRAL CAPSID PROTEIN FUSIONS, PREFERABLY PAPILLOMAVIRUS L1 PROTEINS, AND USES THEREOF

CROSS REFERENCE TO RELATED APPLICATION

This application claims priority from U.S. Provisional Application Ser. No. 60/216,526, filed Jul. 6, 2000, and is incorporated by reference herein in its entirety.

FIELD OF THE INVENTION

The invention provides an efficient means for producing stable viral capsid protein containing vaccines. More specifically, the present invention provides novel vaccines and diagnostic agents for prevention, treatment and/or diagnosis of viral infection, especially papillomavirus infection and cervical cancers associated therewith.

BACKGROUND OF THE INVENTION

Papillomaviruses infect a wide variety of different species of animals including humans. Infection is typically characterized by the induction of benign epithelial and fibroepithelial tumors, or warts at the site of infection. Each species of vertebrate is infected by a species-specific set of papillomavirus, itself comprising several different papillomavirus types. For example, more than sixty different human papillomavirus (HPV) genotypes have been isolated. Papillomaviruses are highly species-specific infective agents. For example, canine and rabbit papillomaviruses cannot induce papillomas in heterologous species such as humans. Neutralizing immunity to infection against one papillomavirus type generally does not confer immunity against another type, even when the types infect a homologous species.

In humans, papillomaviruses cause genital warts, a prevalent sexually-transmitted disease. HPV types 6 and 11 are most commonly associated with benign genital warts condylomata acuminata. Genital warts are very common, and subclinical or inapparent HPV infection is even more common than clinical infection. While most HPV-induced lesions are benign, lesions arising from certain papillomavirus types, e.g., HPV-16 and HPV-18, can undergo malignant progression. Moreover, infection by one of the malignancy-associated papillomavirus types is considered to be a significant risk factor in the development of cervical cancer, the second most common cancer in women worldwide. Of the HPV genotypes involved in cervical cancer, HPV-16 is the most common, being found in about 50% of cervical cancers. The prevalence of HPV-18 ranges from approximately 8-31% depending on the geographical location, and in most areas worldwide, HPV-45 is the third most frequent, oncogenic HPV type (Bosch, F. X., et al. (1995, *J. Natl. Cancer Inst.* 87: 796-802).

In view of the significant health risks posed by papillomavirus infection generally, and human papillomavirus infection in particular, various groups have reported the development of recombinant papillomavirus antigens and their use as diagnostic agents and as prophylactic vaccines. In general, such research has been focused toward producing prophylactic vaccines containing the major capsid protein (L1) alone or in combination with the minor capsid protein (L2). For example, Ghim et al, *Virology*, 190:548-552 (1992), reported the expression of HPV-1 L1 protein, using vaccina expression in Cos cells, which displayed conformational epitopes and the use thereof as a vaccine or for serological typing or detection. This work is also the basis of a patent application, U.S. Ser. No. 07/903,109, filed Jun. 25, 1992 (abandoned in favor of U.S. Ser. No. 08/216,506, filed on Mar. 22, 1994), which has been licensed by the assignee of this application. Also, Suzich et al, *Proc. Natl. Acad. Sci., U.S.A.*, 92:11553-11557 (1995), report that the immunization of canines with a recombinant canine oral papillomavirus (COPV) expressed in a baculovirus/insect cell system completely prevented the development of viral mucosal papillomas. These results are important given the significant similarities between many HPVs and COPV. For example, COPV, similar to HPVs associated with anogenital and genital cancer, infects and induces lesions at a mucosal site. Also, the L1 sequences of COPV shares structural similarities to HPV L1 sequences. Given these similarities, the COPV/beagle model is useful for investigation of L1 protein-containing vaccines, e.g., investigation of the protective immune response, protection from natural infection and optimization of vaccination protocols. (Id.)

Also, a research group from the University of Rochester reported the production of human papillomavirus major capsid protein (L1) and virus-like particles using a baculovirus/insect cell expression system (Rose et al, University of Rochester, WO 94/20137, published on Sep. 15, 1994). In particular, they reported the expression of the L1 major capsid protein of HPV-6 and HPV-11 and the production of HPV-6, HPV-11, HPV-16 and HPV-18 virus-like particles.

Further, a University of Queensland research group also purportedly disclosed the recombinant manufacture of papillomavirus L1 and/or L2 proteins and virus-like particles as well as their potential use as vaccines (Frazer et al, WO 93/02189, published Feb. 4, 1993).

Still further, a United States government research group reported recombinant papillomavirus capsid proteins purportedly capable of self-assembly into capsomere structures and viral capsids that comprise conformational antigenic epitopes (U.S. Pat. No. 5,437,951, Lowy et al, issued Aug. 1, 1995). The claims of this patent are directed to a specific HPV-16 DNA sequence which encodes an L1 protein capable of self-assembly and use thereof to express recombinant HPV-16 capsids containing said HPV-16 L1 protein.

With respect to HPV capsid protein containing vaccines, it is now widely accepted by those skilled in the art that a necessary prerequisite of an efficacious HPV L1 major capsid protein-based vaccine is that the L1 protein present conformational epitopes expressed by native human papillomavirus major capsid proteins (see, e.g., Hines et al, *Gynecologic Oncology*, 53:13-20 (1994); Suzich et al, *Proc. Natl. Acad. Sci., U.S.A.*, 92:11553-11557 (1995)).

Both non-particle and particle recombinant HPV L1 proteins that present native conformational HPV L1 epitopes have been reported in the literature. It is known that L1 is stable in several oligomeric configurations, e.g., (i) capsomeres which comprise pentamers of the L1 protein and (ii) capsids which are constituted of seventy-two capsomeres in a T=7 icosahedron structure. Also, it is known that the L1 protein, when expressed in eukaryotic cells by itself, or in combination with L2, is capable of efficient self-assembly into capsid-like structures generally referred to as virus-like particles (VLPs).

VLPs have been reported to be morphologically and antigenically similar to authentic virions. Also, immunization with VLPs has been reported to elicit the production of virus-neutralizing antibodies. For example, results with a variety of animal papillomaviruses (canine oral papillomavirus and bovine papillomavirus-4) have suggested that immunization with VLPs results in protection against subsequent papillomavirus infection. Consequently, VLPs composed of HPV L1 proteins have been proposed as vaccines for preventing diseases associated with human papillomavirus infections.

Specifically, it has been reported that the L1 protein can assemble into VLPs when expressed using recombinant baculovirus and vaccinia virus vectors and in recombinant yeast (Hagensee et al, *J. Virol.*, 68:4503-4505 (1994); Hofmann et al, *Virology*, 209:506-518 (1995); Kirnbauer et al, *Proc. Natl. Acad. Sci. USA*, 89:12180-12184 (1992); Kirnbauer et al, *J Virol.*, 67:6929-6936 (1993); Rose et al, *J Virol.*, 67:1936-1944 (1993); Sasagawa et al, *Virology*, 206: 126-135 (1995); Suzich et al, *Proc. Natl. Acad. Sci. USA*, 92:11553-11557 (1995); Volpers et al, *Virology*, 200:504-512 (1994); Zhou et al, *J. Virol.*, 68:619-625 (1994)).

Most previous recombinant L1 preparations isolated from eukaryotic cells have resulted in a variable population of VLPs approaching 55 nm in diameter, which are similar in appearance to intact virions. However, VLP assembly is somewhat sensitive to cell type. For example, L1 expressed in *Escherichia coli* is expressed largely in the form of capsomeres or smaller, with few or no capsids apparent either in the cell or upon purification (Rose et al, *J. Virol.*, 67:1936-1944 (1993); L1 et al, *J. Virol.*, 71:2988-2995 (1997)). Similar results are observed when the polyoma virus VP1 protein is expressed in *E. coli* (Salunke et al, *Biophys. J.*, 56:887-900 (1989)).

While eukaryotic cells have been focused on for the production of papillomavirus capsid proteins, and that of other viruses, because of their reported capability to express these proteins and VLPs such that they present appropriate conformational, neutralizing epitopes, there have been some reports of the use of bacteria for the expression of papillomavirus capsid proteins, both in fused and non-fused form, as well as for the manufacture of capsomeres.

For example, it was disclosed in PCT/US98113799, entitled "Homogeneous Human Papillomavirus Capsomere Containing Compositions, Methods for Manufacture, and Use Thereof as Diagnostic, Prophylactic or Therapeutic Agents", that capsomeres expressed in *E. coli* were capable of generating neutralizing antisera in rabbits that prevented papillomavirus infection in a model tissue culture assay. These capsomeres were expressed as non-fusion proteins. Therefore, the expressed L1 proteins did not include any non-PV coding sequences.

Also, L1 et al, *J. Virol.*, 71:2987 (1997) reported the expression of a full length, non-fusion HPV 11 L1 protein in *E. coli* that presented conformational epitopes. However, expression levels were relatively low, and the purification procedure required to isolate the expression product was quite laborious.

Further, Lin et al, *Viriology*, 187:612-619 (1992) reported the expression of CRPV trpE-L1 fusion proteins in *E. coli* and the use of the resultant expression product to induce antisera in rabbits. The fusion protein was expressed in insoluble, refiactile body form, and the insoluble fractions containing the trpE fusion proteins were characterized by SDS-PAGE and the resultant "crude fusion protein" used to immunize rabbits together with an immune adjuvant (MPL and TDM and CWS emulsion) (Ribi Immunochemical Research Inc.(adjuvant)). However, such an impure protein extract would likely be unsuitable for use as a vaccine because of potential endotoxin contamination. Additionally, Lin et al, in *J. Virol.*, 67(7):4154-4162 (1993) reported the expression of CRPV L1 protein in *E. coli* as a TrpE fusion protein. They report therein the identification of neutralizing epitopes and further disclose that a successful papillomavirus vaccine must be based on immunization with full-length, native L1 and that smaller peptides containing major linear epitopes is not feasible.

Still further, Zhang et al, *Virology*, 243:4236-431 (1996) reported the expression of HPV16 L1 proteins in *E. coli*, wherein the L1 sequence was fused at its amino terminus to a 24-amino acid leader sequence, pelB, and the carboxy terminus to six histidine residues (His tag). However, disadvantageously, the bacterial expressed L1 protein was in the form of insoluble aggregates (inclusion bodies) which were expressed at a yield of more than 10% total cell proteins. The insoluble proteins, when isolated with 8M urea and purified by chromatographic separation, after removal of the urea, spontaneously reunited and assembled into polymorphologic aggregations in vitro which included structures resembling native empty capsids as well as incompletely formed capsids. The correctly folded VLPs were purified by sucrose gradient sedimentation, and were recognized by an HPV16 type-specific, conformational monoclonal antibody in an ELISA. However, the purification procedure was quite laborious, which is disadvantageous in the context of vaccine preparation, wherein high protein yields at reasonable cost are necessary.

OBJECTS OF THE INVENTION

It is an object of the invention to solve the problems of the prior art.

More specifically, it is an object of the invention to provide an improved means for producing recombinant viral capsid proteins, that is simple, and which yields viral capsid proteins suitable for use as vaccines, therapeutics and diagnostics. This method is suitable for capsid proteins of both envelope and non-envelope viruses, but is especially preferred for non-envelope viral capsid proteins.

Even more specifically, it is an object of the invention to provide an improved method for producing recombinant papillomavirus capsid proteins, i.e., L1 and/or L2 proteins, that is simple, provides high protein yield, and which results in papillomavirus capsid protein compositions suitable for use as vaccines, therapeutics and diagnostics.

It is a specific object of the invention to provide papillomavirus (PV) capsid proteins, i.e., L1 or L2 proteins, or fragment thereof, fused at their amino or carboxy-terminus to glutathione-5-transferase (GST) protein.

It is another specific object of the invention to express a PV capsid protein or fragment thereof, fused to glutathione-5-transferase (GST) protein, and to purify the resultant capsid-GST fusion by affinity chromatography (glutathione sepharose chromatography.)

It is a more specific object of the invention to express a PV L1 protein as a GST fusion protein and to purify the resultant PV L1-GST fusion by glutathione sepharose chromatography.

It is another specific object of the invention to provide stable viral capsid protein preparations that present native capsid protein conformational, preferably neutralizing epitopes, which are produced by acetone or alcohol precipitation (e.g., ethanol, methanol, butanol) followed by drying to produce a stable powder.

It is another specific object of the invention to produce intact acetone- or alcohol-fixed bacteria that express viral capsid proteins which are suitable for use as diagnostic, therapeutic or prophylactic agents, e.g., veterinary vaccines.

It is a more specific object of the invention to produce intact, acetone- or alcohol-fixed bacteria that express PV capsid proteins, in fused or non-fused form, for use as diagnostic, therapeutic or prophylactic agents.

It is another specific object of the invention to provide a novel method of administering viral capsid protein vaccines, especially non-envelope capsid protein-based vaccines by producing said capsid proteins or bacteria that express said capsid proteins in the form of an acetone- or alcohol-fixed powder that is administered by "blowing" the powder through the skin, or by other aerosol administration routes (e.g., intranasal).

It is another object of the invention to provide storage stable viral capsid protein compositions, especially papillomavirus capsid proteins, in fused or non-fused form, that comprise acetone or alcohol (ethanol or methanol) powders.

It is still another object of the invention to provide intact, acetone-fixed bacteria that express viral capsid proteins, especially PV capsid proteins, that are suitable for use as diagnostic, therapeutic and prophylactic agents.

It is another object of the invention to provide diagnostic kits for detection of viral antibodies that comprise acetone- or alcohol-fixed bacteria or acetone or alcohol powders that contain viral capsid proteins, e.g., PV capsid proteins, that maintain appropriate (native) capsid protein conformation.

BRIEF DESCRIPTION OF THE FIGURES

FIG. 1 is a schematic of the DNA construct used to express a GST-COPV L1 fusion protein in *E. coli.*

FIG. 2 contains results of an ELISA showing that both GST-L1 and purified L1 protein (non-fusion) react with an antibody to a linear (non-conformational) epitope. It can be seen therefrom that the bacterially-expressed L1 proteins display non-conformational epitopes not present on the whole intact virus.

FIG. 3 contains results of another ELISA which shows that the GST-L1 fusion protein and L1 proteins expressed in bacteria also display conformational epitopes based on their specific reactivity with conformational-dependent anti-COPV antibodies.

FIG. 4 contains results of SDS-PAGE gel chromatography. The results indicate that the bacterially expressed GST-L1 and L1 proteins are fairly homogeneous (predominantly found in a single band on SDS gel), with only a slight contamination observable on the GST-L1 protein band.

FIG. 5 contains results of a dog (beagle) study which indicated that the administration of GST-L1 protein at low dosage (1 μg) resulted in complete protection upon challenge.

FIGS. 6A and 6B contain results of ELISA assays which indicate that acetone powders containing GST-L1 fusion proteins react with conformational PV monoclonal antibodies very similarly to non-acetone-fixed GST-L1 fusion proteins.

DETAILED DESCRIPTION OF THE INVENTION

In order to facilitate an understanding of the invention, the following definitions are provided. Otherwise, all technical terms have their ordinary, art-recognized definitions.

Capsid protein: the structural protein of a virus, e.g., enveloped or non-enveloped, which constitutes the capsid structure. Generally, there are several capsid proteins which are often described by whether they are the predominant (major)constituent or lesser (minor) constituent of capsid structure.

Major capsid protein or L1 protein: the structural protein of papillomavirus (PV) which constitutes the major portion of the PV capsid structure. This protein has reported application in the preparation of HPV vaccines and as a diagnostic agent.

Virus-like particles or VLPs: the capsid-like structures which result upon expression and assembly of a papillomavirus L1 DNA sequence alone or in combination with an L2 DNA sequence. VLPs are morphologically and antigenically similar to authentic virions. VLPs may be produced in vivo, in suitable host cells, e.g., mammalian and insect host cells, or may form spontaneously upon purification of recombinant L1 proteins. Additionally, they may be produced using L1 fragments or mutated forms thereof, e.g., L1 proteins that have been modified by the addition, substitution or deletion of one or more amino acids. L1 mutants that fall within the scope of the present invention are those that upon expression present at least one native PV conformational epitope. For example, this includes L1 proteins which have been truncated at the ultimate conserved glutamine residue at the carboxy-terminus. Cleavage at said glutamine residue will remove, on average, 30 to 40 amino acid residues of the L1 protein. Suitable mutants or fragments can be determined based on the reactivity of said L1 proteins with neutralizing antiserum or their ability to elicit neutralizing antiserum.

Correctly-folded L1 protein: L1 protein, fragment thereof, or mutated form thereof, (either monomeric, in the form of small oligomers (dimers-tetramers) or capsomeres), which, upon expression, assumes a conformational structure that presents one or more conformational HPV L1 epitopes present on native viral capsids or VLPs and is suitable for assembly into VLPs. In the present invention, a correctly folded HPV L1 protein will present one or more HPV L1 conformational epitopes.

Conformational L1 HPV epitope: an epitope expressed on the surface of correctly-folded L1 protein which is also expressed by an L1 protein or fragment, or mutated form thereof, which is also expressed by an L1 protein of a corresponding wild-type, infectious HPV. It is well accepted by those skilled in the art that the presentation of conformational epitopes is essential to the efficacy (both as prophylactic and diagnostic agents) of HPV L1 protein immunogens.

Conformational Neutralizing L1 HPV epitope: an epitope expressed on the surface of correctly-folded L1 protein, fragment or mutated form thereof, which is also expressed by an L1 protein of a corresponding wild-type, infectious HPV, and which elicits neutralizing antibodies. It is well accepted by those skilled in the art that the presentation of conformational neutralizing epitopes is essential to the efficacy (both as prophylactic and diagnostic agents) of HPV L1 protein immunogens.

Conformational antibody: an antibody that specifically binds an epitope expressed as a correctly-folded L1 protein but not on denatured L1 protein.

Acetone- or alcohol-fixed viral capsid protein: refers to one or more viral capsid proteins, preferably that of a non-enveloped virus, and more preferably PV, that is precipitated by use of acetone or an alcohol, typically methanol, ethanol or other lower carbon alcohol, and is dried, e.g., by an air drying procedure, to produce a powder that contains stable viral capsid proteins that present native viral capsid protein epitopes, preferably neutralizing epitopes, and which may be stored for prolonged periods under ambient conditions. The resultant powder can be later combined with carriers, excipients, adjuvants, and administered by conventional routes, e.g., injection.

Acetone- or alcohol-fixed bacteria: refers to bacteria that have been treated (fixed) with an alcohol (lower alcohol such as methanol, ethanol or butanol) or acetone, which express on their surface at least one viral capsid protein, and then are dried to a powder. The resultant powder can be later combined with conventional carriers, excipients, adjuvants, and administered by conventional routes, e.g., injection. Alternatively and preferably, the powder is administered by aerosol or by air blowing the powder through the skin.

Mutant enterotoxin: this refers to mutant forms of bacterial endotoxins, especially *E. coli* heat-labile enterotoxin, that have lost their toxicity but retained immunological activity which are useful as adjuvants when administered with other antigens, especially in oral vaccines. (See U.S. Pat. No. 6,019,982, issued Feb. 1, 2000, to Clements and assigned to Tulane University, incorporated by reference herein.)

Capsomere: this refers to a structure that makes up the larger viral capsid structure that is generally a polymer of one or more types of capsid proteins. In the case of PV, a native capsomere comprises a pentamer of L1 capsid proteins.

Capsid: this refers to the structural portion of a virus, e.g., PV, that is comprised of capsomeres. In the case of PV, the viral capsid is comprised of 72 capsomeres.

The present invention provides a highly efficient method for producing viral capsid proteins at high yield, which utilizes a fairly simple, straight-forward purification scheme, which results in viral capsid proteins that present appropriate conformational, neutralizing epitopes, which viral capsid proteins may be stored for prolonged periods of time at room temperature, and which are administrable by air injection or aerosol methods, as well as conventional methods including of course injection routes.

In a preferred embodiment, as exemplified herein, the present invention will be used to produce stable PV capsid protein compositions, i.e., PV L1 and L2 proteins in fused or non-fused form, as well as truncated versions thereof, that retain conformational epitopes. However, it is anticipated that the methods herein can be extrapolated to other viral capsid proteins, especially capsid proteins of other non-enveloped viruses that are similar to papillomavirus, or that of enveloped-viruses.

As discussed previously, while there are several L1 protein vaccines in clinical trials, the cost of these preparations is very expensive for one or more of the following reasons:

(1) production typically requires the use of cesium chloride gradients for purification of virus-like particles;

(2) virus-like particles tend to be inherently unstable and therefore must be maintained in a frozen state to prevent disassembly;

(3) production of L1 virus-like particles is typically effected in baculovirus or yeast systems which are generally more expressive or difficult to work with than bacterial expressive systems; and (4) VLP preparations are frequently contaminated with nucleic acids and other proteins.

The present inventors have developed a purification and expression procedure that should obviate all of these problems and obstacles.

In one aspect, the present invention relates to the expression of a viral capsid protein, preferably that of a non-enveloped virus, and most preferably a papillomavirus L1 or L2 capsid protein or fragment thereof as a glutathione-S-transferase (GST) fusion protein. The GST protein may be fused at the amino-terminal or carboxy-terminal portion of the viral capsid protein or fragment thereof. In preferred embodiments, the GST protein is fused to the amino terminus of an intact or carboxy-truncated PV L1 protein. However, it is hypothesized that fusion to the carboxy-terminus or amino-truncated L1 fragments will also yield capsid proteins that express one or more conformational, preferably neutralizing, epitopes.

Fusion of GST to viral capsid proteins such as PV L1 proteins is advantageous in that the expression product can easily be purified by glutathione sepharose chromatography. At least in the case of GST-COPV L1 fusions, it has been shown that the resultant fusion protein results in pentamers (capsomeres) that do not self-assemble into higher order structures in vitro (VLPs). It is hypothesized that self-assembly into VLPs does not occur because fusion of the GST protein to the amino-terminus may block residues contained in the amino-terminal portion of the PV L1 protein that may be critical for VLP formation or because the L1 protein is truncated at its carboxy-terminus. Accordingly, it is possible that, if the GST protein is alternatively fused at the carboxy-end of the PV L1 protein, assembly into higher order structures, including VLPS, may occur.

As capsomeres which express conformational epitopes may be superior to VLPs in the context of vaccine preparation (e.g., because of their smaller size which may facilitate in vivo administration), it may be preferred to fuse the GST protein to the amino terminal protein of the L1 protein rather than the carboxy terminus. However, this is not critical to the present invention, and whether the particular viral capsid protein or fragment is fused to GST at its amino-terminus or carboxy terminus is an arbitrary design choice.

Another aspect of the invention relates to novel stable forms of viral capsid proteins. In particular, the present invention provides novel acetone- or alcohol-fixed viral capsid proteins or acetone- or alcohol-fixed intact microbial cells, preferably bacteria, and more preferably *E. coli* that express at least one capsid protein on their surface. Fixation essentially comprises the addition of the acetone or alcohol solvent (e.g., methanol), typically under cold conditions, to produce a capsid protein or whole microbial containing precipitation, which is then dried to a powder-like consistency. It has been demonstrated in the case of COPV L1 capsid protein that both acetone-fixed COPV capsid proteins and acetone-fixed intact *E. coli* (that express COPV L1), when later reconstituted in a carrier (phosphate buffered solution) present conformational, neutralizing epitopes. These results indicate that the fixation procedure retains the authentic viral capsid protein structure, at least to the extent that some (and potentially all) conformational, neutralizing epitopes are preserved.

This discovery is unparalleled in the context of vaccine development as well as diagnostic applications, as the present invention provides a relatively quick, easy procedure to produce viral capsid proteins that substantially retain their authentic (native) viral capsid protein structure. Moreover, in the case of fixed-intact microbia, the procedure is even more practical as it eliminates the need to recover the capsid protein from the microbia, e.g., *E. coli*. This is particularly suitable in veterinary contexts.

However, it may even be suitable in the context of human vaccines, as methods for inactivating bacterial enterotoxins, e.g., by mutagenesis are known. In fact, the use of such mutated enterotoxins as adjuvants has been reported and is the subject of a number of patents assigned to Tulane University.

Examples of viruses that contain capsid proteins that may be acetone- or alcohol-fixed include both enveloped and non-enveloped viruses. Preferably, such viruses will include papovaviruses, such as papillomaviruses, Jc virus, and others; rotaviruses and orbiviruses, reoviruses, picornaviruses (e.g., polia, hepatitis A, coxsackieviruses, enteroviruses, rhinoviruses), parvoviruses, adenoviruses, hepadnaviruses, calciviruses, HIV, and other retroviruses, and prototype viruses such as VSV and rabies virus. This list is meant to be exemplary and not exhaustive of viral capsid proteins that may be treated (fixed) according to the invention.

Also, while the invention is preferably directed to acetone- or alcohol-fixed viral capsid proteins, the technique should be applicable for fixation of other viral proteins, e.g., proteases, and other viral enzymes, such as transcriptases, polymerases, and other kinases.

The manner by which acetone- or alcohol-fixation is achieved may be varied within wide limits. All that is necessary is the addition of a sufficient amount of the acetone or alcohol solvent, e.g., a lower alcohol such as methanol, ethanol, propanol, butanol, pentanol, hexanol, to result in precipitation of the VLP or microbial cell containing the microbia, which can be dried to produce a powder that contains the VLP or VLP-expressing microbial cell in a form whereby it can be stored for prolonged periods under ambient conditions. This is a significant advantage as it will enable the materials to be shipped to Third World Countries that may not otherwise have adequate storage capabilities.

As explained, the present invention is applicable for producing viral capsid proteins for different viruses, especially papillomavirus and, in particular, any human papillomavirus. Many HPV L1 and L2 DNAs have been reported in the literature and are publicly available. (See, e.g., Baker, Sequence Analysis of Papillomavirus, *Genomes, pp.* 321-384; Long et al, U.S. Pat. No. 5,437,931, Cole et al, *J Mol. Biol.*, 193:599-608 (1987); Danos et al, *EMBO J.*, 1:231-236 (1982); Cole et al *J. Virol.*, 38(3):991-995 (1986)). Also, it is well known that HPV L1 DNAs exhibit significant homology. Therefore, a desired HPV L1 DNA can easily be obtained, e.g., by the use of a previously reported HPV L1 DNA or a fragment thereof as a hybridization probe or as a primer during polymerization chain reaction (PCR) amplification. Indeed, numerous HPV L1 DNAs have been cloned and expressed.

Preferably, the HPV L1 DNA said in the subject invention will be derived from an HPV which is involved in cancer or condylomata acuminata, e.g., HPV-16, HPV-18, HPV-31, HPV-33, HPV-35, HPV-39, HPV-45, HPV-51, HPV-52, and HPV-56 are involved in cancer, and HPV-6, HPV-11, HPV-30, HPV-42, HPV-43, HPV-44, HPV-54, HPV-55, and HPV-70, are involved in warts. However, the subject capsid proteins may be produced using any desired HPV L1 DNA.

As noted, the subject capsid protein DNA or fragment, fused or non-fused, will be expressed preferably in a prokaryotic microbial host, e.g., bacteria such as *E. coli*, that can be cultured under conditions that favor the production of capsid proteins. This will largely depend upon the selected host system and regulatory sequences contained in the vector, e.g., whether expression of the capsid protein requires induction.

HPV L1 sequences or other capsid protein DNAs may be expressed in any host cell that provides for the expression of recoverable yields of the capsid protein in appropriate conformation. Suitable host systems for expression of recombinant proteins are well known and include, by way of example, bacteria, mammalian cells, yeast, and insect cells. A preferred expression system comprises the *E. coli* expression system used in the Examples, as this system provides for high capsomere yields. However, HPV L1 and L2 proteins, as well as other viral capsid proteins, can be produced in other systems.

Suitable vectors for cloning of expression of the subject HPV L1 encoding DNA sequences are well known in the art and commercially available. Further, suitable regulatory sequences for achieving cloning and expression, e.g., promoters, polyadenylation sequences, enhancers and selectable markers are also well known. The selection of appropriate sequences for obtaining recoverable protein yields is routine to one skilled in the art.

Viral capsid proteins and capsomeres have application in prophylactic vaccines and diagnostics. The subject PV capsomeres may be advantageous thereto because of their homogeneity and stability.

As discussed, the present invention should be broadly applicable to any HPV L1 sequence. Also, in the acetone- or alcohol-fixation aspect of the invention, the subject methods are potentially applicable to any viral capsid protein or microbia that expresses such capsid protein. As noted previously, there are a variety of HPV types known in the art. Further, particular types of HPVs are associated with particular infections such as flat warts, cutaneous warts, epidermodysplasia verruciformis, lesions and cervical cancer. Over sixty different HPV types have been identified in clinical lesions by viral nucleotide sequence homology studies. See, e.g., Jenson et al, In: Belshe, R. ed., Textbook of human virology, Second Edition, MASS:PSG, 1989:—951, and Kremsdorf et al, *J. Virol.*, 52:1013-1018 (1984). The HPV type determines, in part, the site of infection, the pathological features and clinical appearance as well as the clinical course of the respective lesion.

Because it is believed that there is little or no cross-immunity for HPV types and immunity to infection is HPV type-specific, it will be necessary to produce recombinant HPV L1 capsid protein for each specific HPV type upon which protection or treatment is needed. However, due to the homology between the L1 proteins and genes, hybridization techniques can be utilized to isolate the particular L1 gene of interest. Nucleotide probes selected from regions of the L1 protein which have been demonstrated to show sequence homology, can be utilized to isolate other L1 genes. Methods for hybridization are known in the art. (See, e.g., *Nucleic Acid Hybridization, A Practical Approach*, IRL Press, Washington, D.C. (1985); *Molecular Cloning, A Laboratory Manual*, Maniatis et al, eds., Cold Spring Harbor Laboratory, Cold Spring Harbor, N.Y. (1982); and *Molecular Cloning, A Laboratory Manual*, Sambrook et al, eds., Cold Spring Harbor Laboratory, Second Edition, Cold Spring Harbor, N.Y. (1989.)) Alternatively, PCR methods can be utilized to amplify L1 genes or gene fragments. (See, e.g., U.S. Pat. Nos. 4,683,195; 4,683,202; and 4,800,159).

Virus particles can also be isolated for a particular papillomavirus type, the DNA cloned, and the nucleic acid sequences encoding L1 proteins isolated. Methods for isolation of viral particles and cloning of virus DNAs have been reported. (See, e.g., Heilman et al, *J. Virology*, 36:395-407 (1980); Beaudenon et al, *Nature*, 321:246-249 (1986); Georges et al, *J. Virology*, 51:530-538 (1984); Kremsdorf et al, *A. Virology*, 52:1013-1018 (1984); Clad et al, *Virology*, 118:254-259 (1982); DeVilliers et al, *J. Virology*, 40:932-935 (1981); and European Patent Application 0,133,123.))

Alternatively, the L1 protein for a particular human papillomavirus can be isolated, the amino acid sequence determined and nucleic acid probes constructed based on the predicted DNA sequence. Such probes can be utilized in isolating the L1 gene from a library of the papillomavirus DNA. (See, e.g., Suggs et al, *PNAS,* 78(11):6613-6617 (1981) and Young and Davis, PNAS, 80:1194 (1983).)

In the acetone or alcohol fixation aspect of the invention, it is possible to use baculovirus vectors for expression. Baculovirus systems offer the advantage that a large percentage of cells can be induced to express protein due to the use of infection rather than transfection techniques. While baculovirus is an insect virus and grows in insect cells (Sf9), these cells retain many of the eucaryotic mechanisms for processing of proteins including glycosylation and phosphorylation which may be important for generating proteins of appropriate conformation. Baculovirus vector systems are known in the art. (See, e.g., Summers and Smith, *Texas Agricultural Experimental Bulletin,* No. 1555 (1987); Smith et al, *Mol. Cell. Biol.,* 3:2156-2165 (1985); Posse, *Virus Research,* 5:4359 (1986); and Matsuura, J. Gen. Virol., 68:1233-1250 (1987).) Also, it has been reported that baculovirus-infected cells express HPV L1 proteins exhibiting the appropriate conformation. However, for the reasons already identified, bacterial expression and, more preferably, expression in *E. coli*, of a GST-L1 protein fusion is preferred.

For expression in an appropriate expression system, an L1 gene or modified L1 gene is operably linked into an expression vector and introduced into a host cell to enable the expression of the L1 protein by that cell. The gene with the appropriate regulatory regions will be provided in the proper orientation and reading frame to allow for expression. Methods for gene construction are known in the art. (See, in particular, *Molecular Cloning, A Laboratory Manual,* Sambrook et al, eds., Cold Spring Harbor Laboratory, Second Edition, Cold Spring Harbor, N.Y. (1989), and the references cited therein.)

A wide variety of transcriptional and regulatory sequences may be employed. The signals may be derived from viral sources, where the regulatory signals are associated with a particular gene which has a high level of expression. That is, strong promoters, for example, strong bacterial, viral or mammalian promoters may be utilized. In this manner, the optimum conditions for carrying out the invention include the cloning of the L1 gene into an expression vector that will overexpress conformationally-dependent virus-neutralizing epitopes of the L1 protein in transfected or infected target cells (*E. coli.*)

The suitability of the viral capsid proteins, preferably HPV capsid proteins, produced according to the invention for use as vaccines or as diagnostic agents can be confirmed by reaction with antibodies or monoclonal antibodies which react or recognize conformational epitopes present on the intact virion and based on their ability to elicit the production of neutralizing antiserum. Suitable assays for determining whether neutralizing antibodies are produced are known to those skilled in the art. This is an essential characteristic of HPV capsid proteins or other viral capsid proteins which are to be used in HPV or other viral vaccines. In this manner, it can be verified whether the HPV capsid proteins will elicit the production of anti-HPV neutralizing antibodies. Thus, other expression vectors and expression systems can be tested for use in the invention.

As discussed, the capsid proteins and stable forms thereof produced according to the present invention can be utilized to detect, diagnose, serotype, and treat papillomavirus infection. When used for diagnosis or serotyping, capsid proteins, e.g., HPV capsid proteins produced according to the invention may be labeled using any of a variety of labels and methods of labeling. Examples of types of labels which can be used in the present invention include, but are not limited to, enzyme labels, radioisotopic labels, non-radioactive isotopic labels, fluorescent labels, toxin labels, and chemiluminescent labels.

Examples of suitable enzyme labels include malate hydrogenase, staphylococcal nuclease, delta-5-steroid isomerase, yeast-alcohol dehydrogenase, alpha-glycerol phosphate dehydrogenase, triose phosphate isomerase, peroxidase, alkaline phosphatase, asparaginase, glucose oxidase, beta-galactosidase, ribonuclease, urease, catalase, glucose-6-phosphate dehydrogenase, glucoamylase, acetylcholineesterase, etc.

Examples of suitable radioisotopic labels include $^3$H, $^{125}$I, $^{131}$I, $^{32}$P, $^{35}$S, $^{14}$C, $^{51}$Cr, $^{57}$To, $^{58}$Co, $^{59}$Fe, $^{75}$Se, $^{152}$Eu, $^{90}$Y, $^{67}$Cu, $^{211}$At, $^{212}$Pb, $^{47}$Sc, and $^{109}$Pd.

Examples of suitable fluorescent labels include a $^{152}$Eu label, a fluorescein label, an isothiocyanate label, a rhodamine label, a phycoerythrin label, a phycocyanin label, an allophycocyanin label, an o-phthaldehyde label, a fluorescamine label, etc.

Examples of suitable toxin labels include diphtheria toxin, ricin, and cholera toxin. Examples of chemiluminescent labels include a luminal label, an isoluminal label, an aromatic acridinium ester label, an imidazole label, and acridinium salt label, an oxalate ester label, a luciferin label, a luciferase label, an aequorin label, etc.

Those of ordinary skill in the art will know of other suitable labels which may be employed in accordance with the present invention. The binding of these labels to viral capsid proteins, e.g., in the form of capsomeres, can be accomplished using standard techniques commonly known to those of ordinary skill in the art. Typical techniques are described by Kennedy et al, *Clin. Chim. Acta,* 70:1-31 (1976), and Schurs et al, *Clin. Chim. Acta,* 81:1-40 (1977). Coupling techniques mentioned in the latter are the glutaraldehyde method, the periodate method, the dimaleimide method, the m-maleimidobenzyl-N-hydroxy-succinimide ester method, all these methods incorporated by reference herein.

The detection of the anti-1HPV antibodies using the subject capsid proteins can be improved through the use of carriers. Well-known carriers include glass, polystyrene, polypropylene, polyethylene, dextran, nylon, amylases, natural and modified celluloses, polyacrylamides, agaroses and magnetite. The nature of the carrier can be either soluble to some extent or insoluble for the purposes of the present invention. Those skilled in the art will note many other carriers suitable for binding proteins, or will be able to ascertain the same by use of routine experimentation.

The most important aspect of the present invention, however, involves the development of viral vaccines, preferably PV vaccines. The vaccines of the invention will contain an amount of the subject viral capsid proteins, e.g., in acetone- or alcohol-fixed form sufficient to induce formation of neutralizing antibodies in the host contained in a pharmaceutically acceptable carrier.

Administration of the subject capsid protein-containing vaccines may be effected by any pharmaceutically acceptable means, e.g., parenterally, locally or systemically, including by way of example, oral, intranasal, intravenous, intramuscular, and topical administration. The manner of administration is affected by factors including the natural route of infection. As noted in the case of acetone- or alcohol-fixed capsid proteins, the preferred route of administration is by blowing through the skin as by use of aerosol. The dosage administered will depend upon factors including the age, health, weight, kind of concurrent treatment, if any, and nature and type of the particular viral, e.g., human, papillomavirus. The vaccine may be employed in dosage form such as capsules, liquid solutions, suspensions, or elixirs, for oral administration, or sterile liquid formulations such as solutions or suspensions for parenteral or intranasal use. An inert, immunologically acceptable carrier is preferably used, such as saline or phosphate-buffered saline.

The vaccines will be administered in therapeutically effective amounts. That is, in amounts sufficient to produce a protective immunological response. Generally, the vaccines will be administered in dosages ranging from about 0.1 mg protein to about 20 mg protein, more generally about 0.001 mg to about 100 mg protein. Single or multiple dosages can be administered.

As noted, the invention further embraces the production of capsid protein fragments that upon expression present conformational, neutralizing epitopes. These fragments will include internal, carboxy- and amino-terminal deletions. The deletion may range in size from 1 to about 100 amino acids, more preferably 1 to 50 amino acids, and most preferably from about 1 to 25 amino acids. It is essential that the deletion still allow for the expression of a capsid protein, e.g., HPV L1 protein, that when expressed in fused or non-fused form presents at least one conformational, neutralizing epitope.

The method of the present invention makes possible the preparation of capsid proteins containing vaccines, e.g., HPV capsid protein-containing vaccines, suitable for preventing virus infection, e.g., PV infection. By following the methods of the invention, vaccines for any of human specific papillomavirus can be made.

As more than one PV type may be associated with PV infections, the vaccines may comprise stable HPV capsid proteins derived from more than one type of PV. For example, as HPV 16 and 18 are associated with cervical carcinomas, therefore a vaccine for cervical neoplasia may comprise VLPs of HPV 16; of HPV 18; or both HPV 16 and 18.

In fact, a variety of neoplasia are known to be associated with PV infections. For example, HPVs 3a and 10 have been associated with flat warts. A number of HPV types have been reported to be associated with epidermodysplasia verruciformis (EV) including HPVs 3a, 5, 8, 9, 10, and 12. HPVs 1, 2, 4, and 7 have been reported to be associated with cutaneous warts and HPVs 6b, 11a, 13, and 16 are associated with lesions of the mucus membranes (see, e.g., Kremsdorf et al, *J. Virol.*, 52:1013-1018 (1984); Beaudenon et al, *Nature*, 321:246-249 (1986); Heilman et al, *J. Virol.*, 36:395-407 (1980); and DeVilliers et al, *J. Virol.*, 40:932-935 (1981)). Thus, the subject vaccine formulations may comprise a mixture of capsid proteins or fragments derived from different HPV types depending upon the desired protection.

As indicated, the HPV capsid proteins of the invention can also be utilized for serotyping and for incorporation in serotyping kits.

For serological testing, the kits will comprise the subject viral capsid proteins and means for detection such as enzyme substrates, labeled antibody, and the like.

Having now generally described the invention, the following examples are offered by way of illustration and not intended to be limiting unless otherwise specified.

EXAMPLE 1

Figure 1:
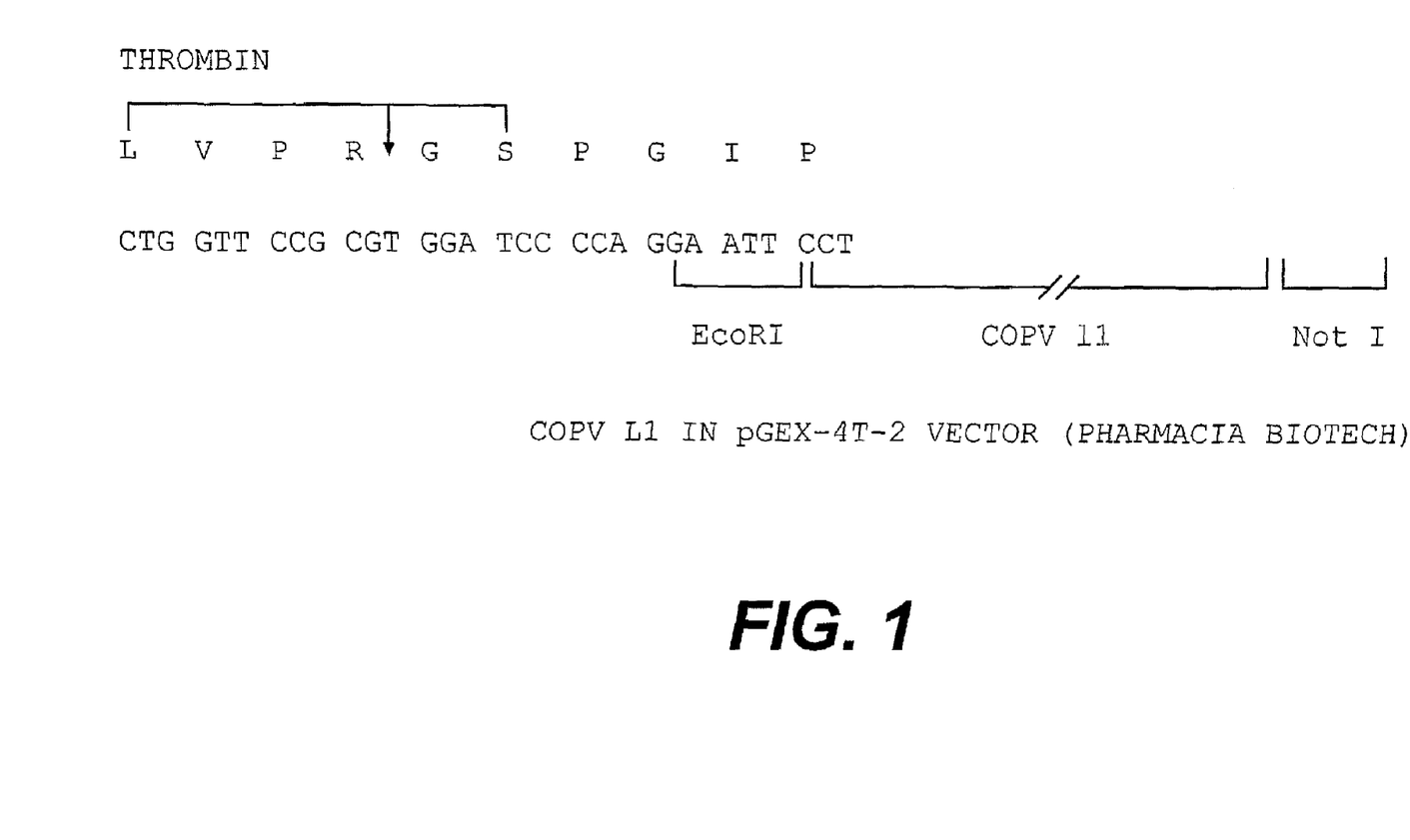

A COPV GST L1 fusion protein was expressed using the pGEX-4T-2 vector available from Pharmacia Biotech in *E. coli*. A schematic of the DNA construct used is contained in FIG. 1. Essentially, a COPV L1 protein lacking 26 amino acids at the carboxy-terminal portion of the L1 protein was fused at its amino terminus with a glutathione-5-transferase (GST) protein tag. The presence of the GST tag is advantageous as it allows for the resultant fusion proteins to be recovered by affinity chromatography.

This is effected by the use of an affinity column that specifically binds the GST protein (glutathione sepharose column). During purification, it is observed that the GST COPV L1 protein is associated with the bacterial Gro EL protein. Accordingly, a series of steps are effected to dissociate the bacterial Gro EL protein from the GST L1 fusion protein.

However, it should be noted that the particulars of this purification procedure is not essential to the invention. In fact, the GST-L1 protein was recovered from the column under conditions that were quite harsh. For example, the purification procedure included two non-denaturing urea elution steps wherein the affinity column was washed with urea. It is anticipated by the inventors that purification and recovery will be able to be effected under less harsh conditions, by routine optimization of the purification process, e.g., by the use of different eluting agents, or pH conditions. Indeed, this purification procedure is merely exemplary of purification procedures that can be used. However, it demonstrates that an efficacious (protective) COPV GST-L1 capsomeres can be obtained from *E. coli*.

When examined by electron microscopy, it was seen that the GST-L1 fusion proteins were present as pentamers that did not self-assemble into higher order structures in vitro. It is speculated that assembly may not occur because amino acid residues at the amino-terminus of the COPV L1 protein may be involved in assembly of VLP structures, or because of the fact that the expressed L1 protein was carboxy-truncated.

EXAMPLE 2

Reactivity of GST-L1 Fusion with Linear Antibodies

Figure 2:
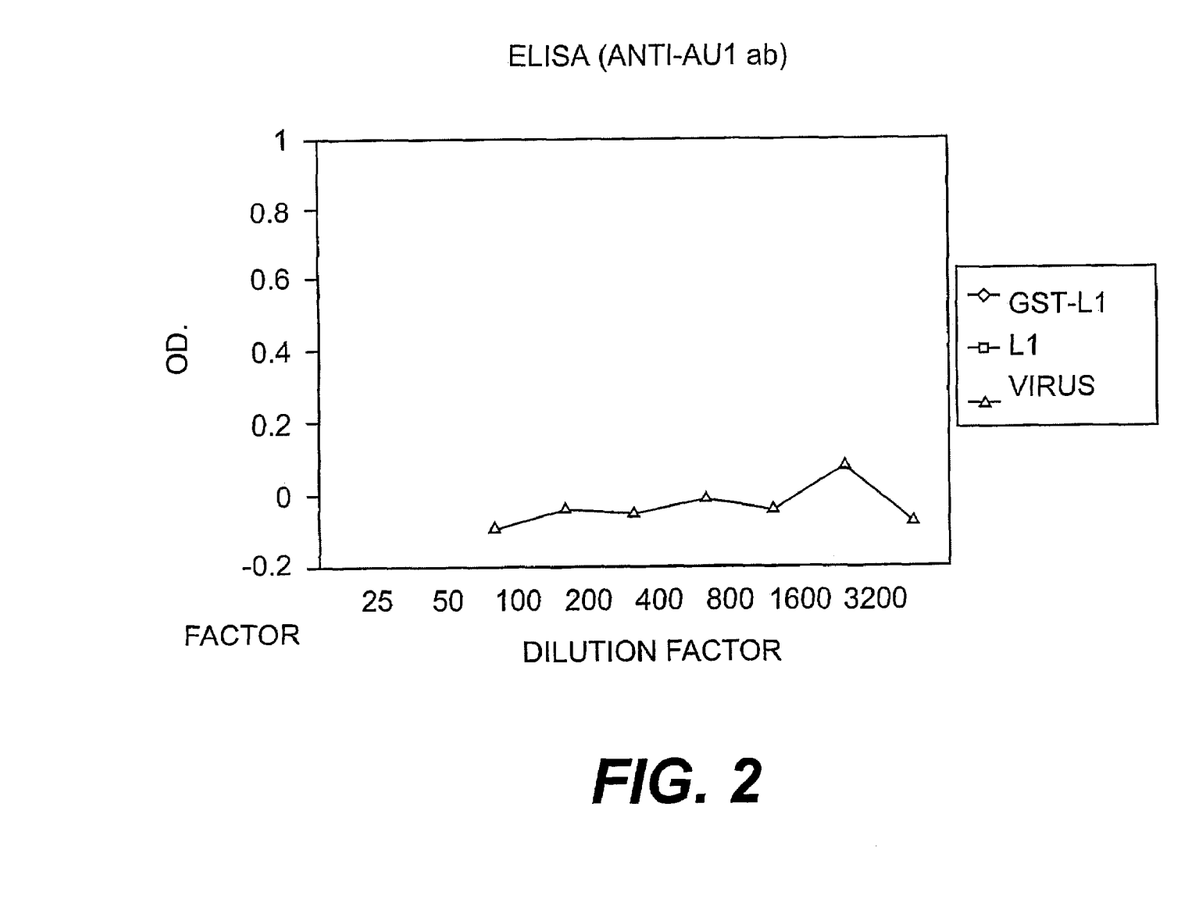

The reactivity of the COPV L1-GST fusion with linear antibodies was tested. As shown in FIG. 2, the purified GST-L1 capsomeres reacted with an antibody (anti-AV 1 Ab) to a linear (non-conformational epitope). Therefore, the ELISA results in FIG. 2 indicate that the GST-L1 fusion protein expresses non-conformational epitopes) which are not present on whole, intact virus.)

EXAMPLE 3

Figure 3:
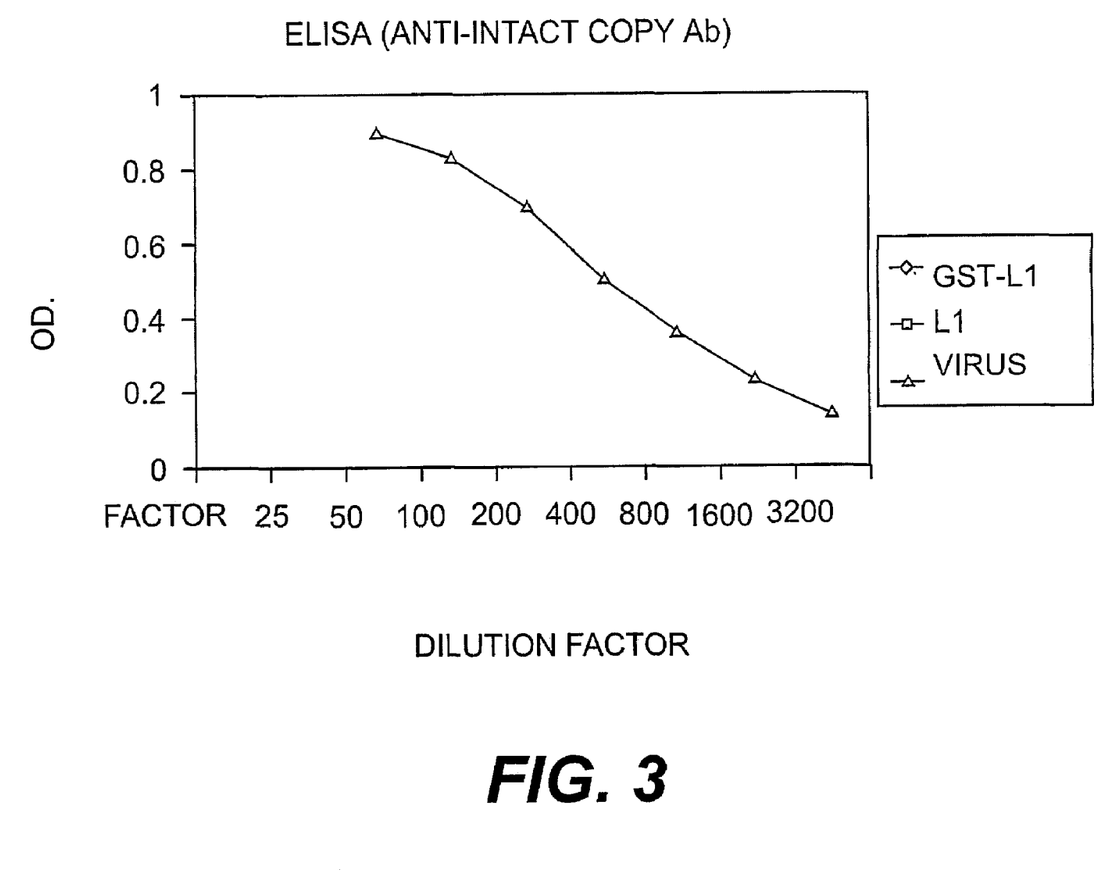

It was also determined whether the GST-L1 fusion protein reacted with conformational monoclonal antibodies specific to conformational epitopes on COPV L1 protein. As shown in FIG. 3, it was surprisingly found that the GST-COPV L1 fusion reacted with an antibody produced against intact (conformationally correct) COPV L1 protein. As expected, and as can be seen from the ELISA results, the positive control, i.e., intact COPV virus, also reacted with the anti-intact COPV antibodies. Thus, the GST-L1 fusion protein apparently expresses both linear and conformational epitopes. The presence of linear epitopes may be attributable to the purification procedure which includes two urea washing procedures which may result in some protein denaturation.

EXAMPLE 4

Purity of COPV GST-L1 Fusion

Figure 4:
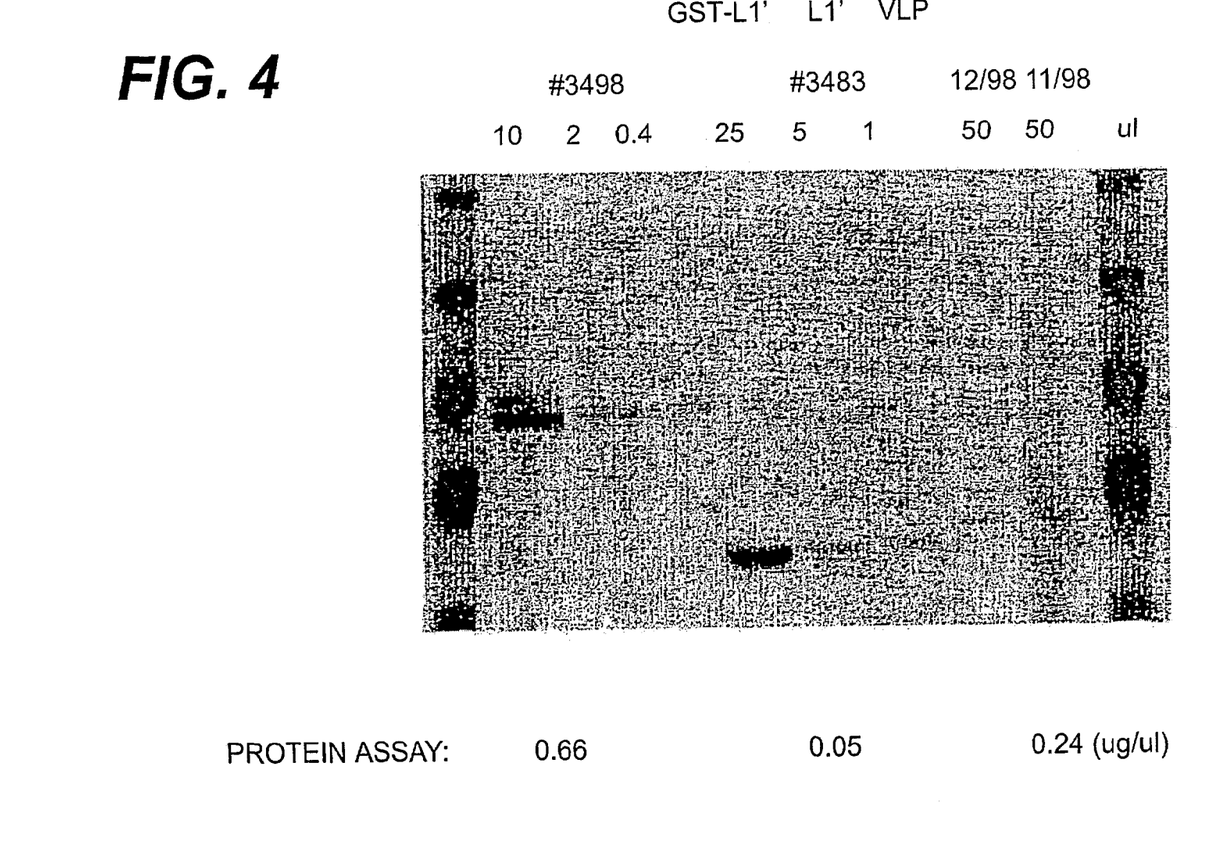

As shown in FIG. 4, when the COPV GST-L1 and COPV L1 proteins were applied to an SDS gel electrophoresis column, they were present predominantly as a single band. However, as can be seen from the figure, there was a slight contamination in the GST-L1 composition. Based on these results, it would appear that the affinity purified GST-L1 fusion is relatively homogeneous.

EXAMPLE 5

Use of GST-COPV L1 Fusion as an Immunogen

Figure 5:
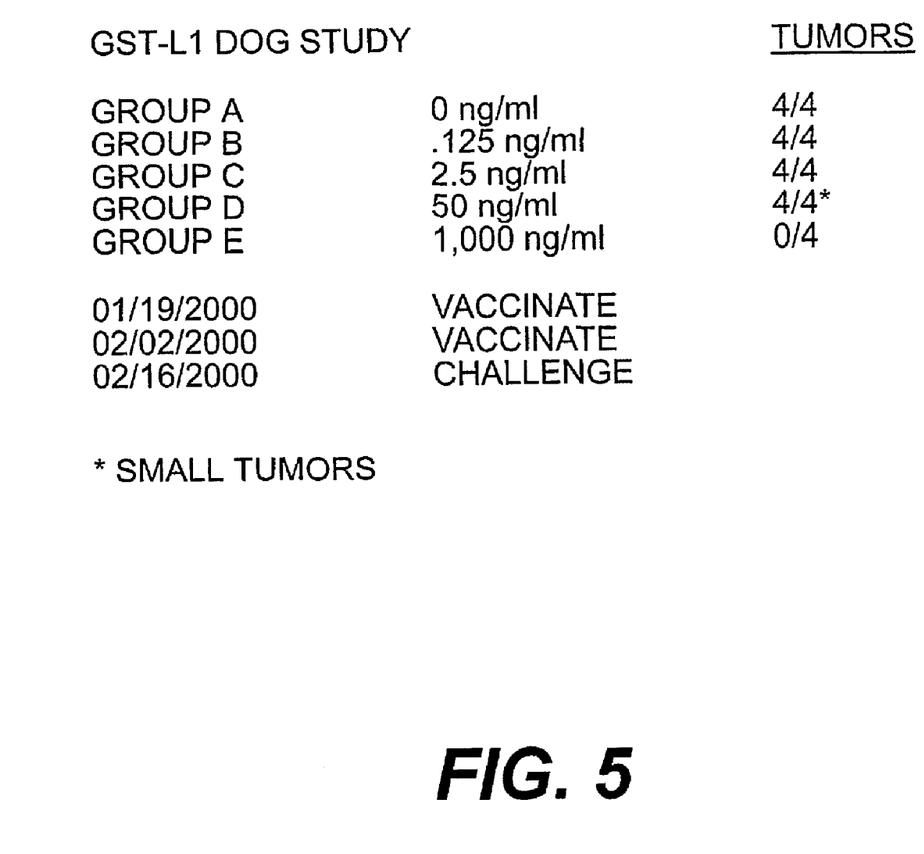

As shown by the results in FIG. 5, administration of the GST-L1 fusion contained in phosphate buffered saline (PBS) at a 1 µg dosage resulted in complete protection in beagle dogs upon challenge. These results are truly unexpected, and provide compelling evidence that GST-L1 fusion proteins are suitable for use in PV vaccine compositions.

EXAMPLE 6

Identical amounts of the purified GST-L1 fusion protein (contained in PBS) utilized in the previous Example were obtained. One aliquot was kept on ice and the other precipitated using ice-cold acetone and the precipitate air-dried to a powder. The resultant powder was then resolubilized in the original volume of PBS.

Figure 6A:
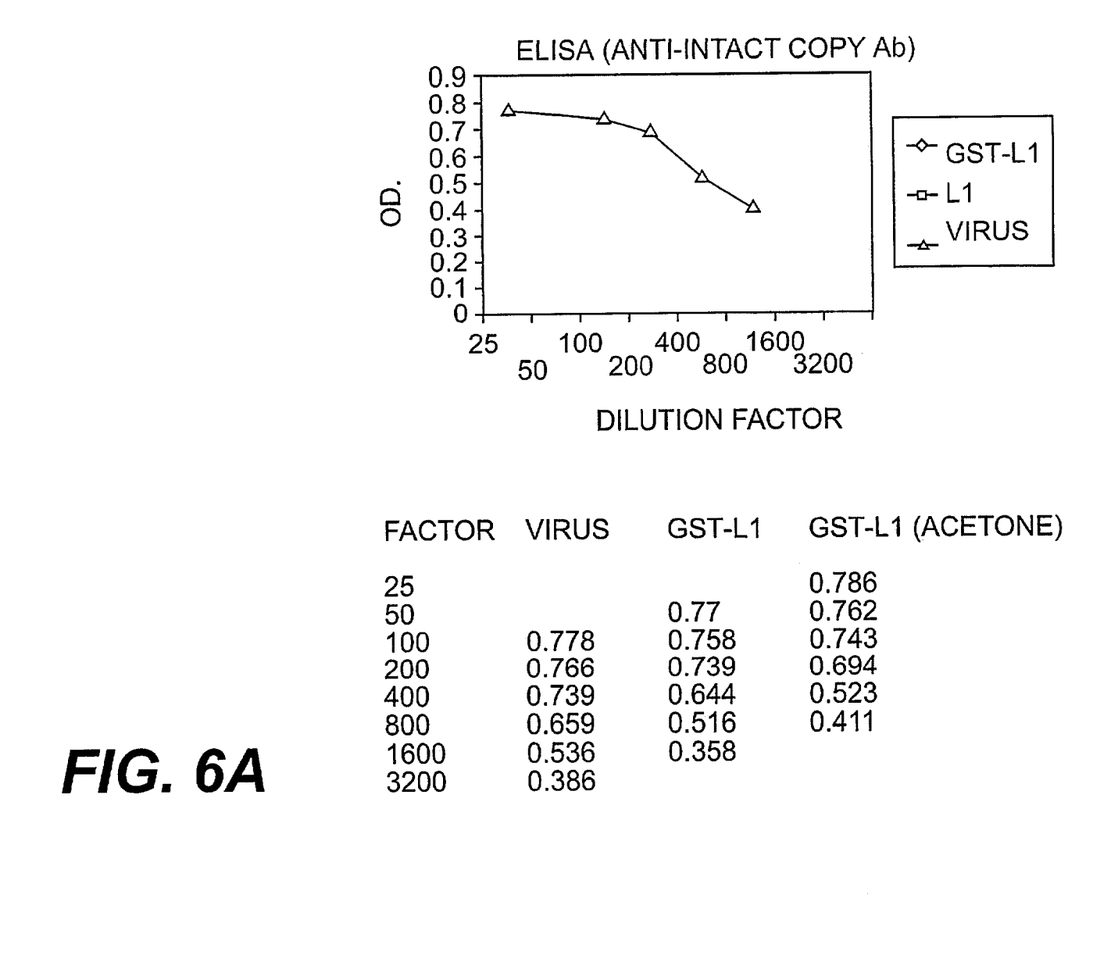
Figure 6B:
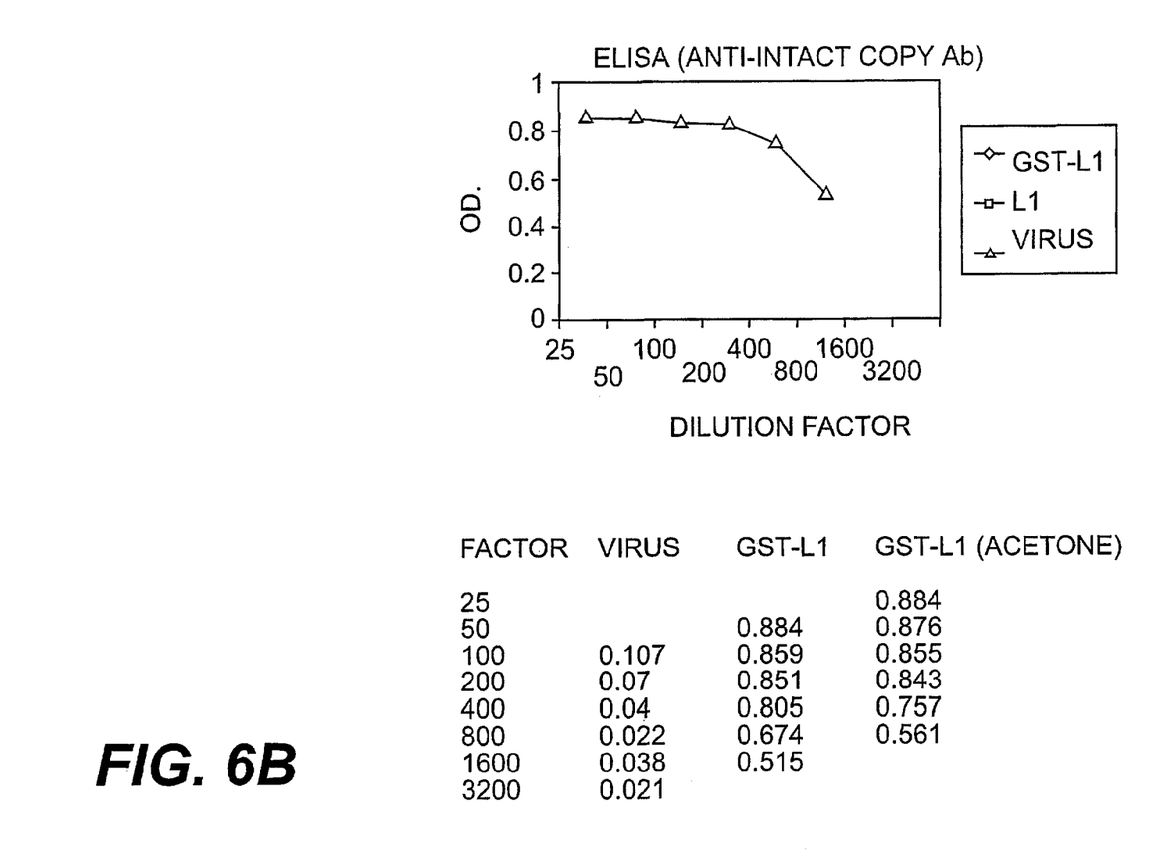

Thereafter, the immunoreactivity of the reconstituted GST-L1 acetone powder to the original purified GST-L1 protein were compared with different conformational antibodies by ELISA. As can be seen from the results in FIG. 6, the GST-L1 protein contained in the acetone powder retained conformational epitopes. Also, intact acetone-fixed *E. coli* also were fused to react with such antibodies.

These results indicate that it is feasible to prepare acetone- or alcohol-fixed powders of purified GST-L1 (or other viral capsid proteins in fused or non-fused form), or of bacteria which express L1 or GST-L1 fusions, or fragments thereof, that present conformational epitopes. These acetone or alcohol powders should be well suited for use as prophylactic or protective viral vaccines or as diagnostic agents because they should elicit or specifically bind antibodies directed against conformational, neutralizing epitopes on the authentic capsid protein.

As discussed previously, this is advantageous for several reasons. First, acetone- or alcohol-fixed capsid protein powders can be stored under ambient conditions for prolonged periods of time. This is a significant benefit as it should allow for vaccines to be delivered to third world countries and stored at relatively low cost. For example, this approach may allow for the production of other acetone stabilized capsid protein vaccines, particularly for other non-enveloped capsid protein containing viruses.

Second, it will be advantageous from an administration perspective because the subject acetone- or alcohol-fixed powder vaccines can be administered, e.g., by air injection, through the skin, or by use of aerosol methods. Suitable devices for blowing such powders through the skin are commercially available. For human recipients, acetone-fixed immunogens preferably will be produced by fixation of a viral capsid protein, or fragment, in fused or non-fused form, e.g., a GST-L1 fusion, that is then administered to human subjects, preferably by air injection.

In the case of animal recipients, the administered vaccine may comprise either an acetone powder of the purified capsid protein, fused or non-fused, or may comprise an acetone- or alcohol-fixed powder produced from the intact bacteria that expresses the capsid protein, fused or non-fused, preferably which has been treated to neutralize endotoxins and other contaminants.

What is claimed is:

1. A method of treating and/or preventing papillomavirus infection comprising administering a therapeutically or prophylactically effective amount of a fusion protein comprising a human papillomavirus L1 capsid protein or fragment thereof fused at its amino—or carboxy—terminus to a glutathione-transferase (GST) protein, wherein said fusion protein has at least one conformational epitope expressed by a native papillomavirus capsid protein.

2. The method of claim 1, wherein said GST protein is fused at the amino-terminus of the capsid protein.

3. The method of claim 1, wherein said capsid protein is an L1 protein or fragment thereof.

4. The method of claim 1, wherein said human papillomavirus L1 protein is selected from the group consisting of HPV-1, HPV-6, HPV-16, HPV-18, HPV-33, and HPV-35 L1 protein.

5. The method of claim 1, wherein said fusion protein is acetone- or alcohol-fixed.

* * * * *